United States Patent [19]

Kaplan

[11] Patent Number: 4,603,105
[45] Date of Patent: Jul. 29, 1986

[54] EFFICIENT SCREENING METHODS FOR LOW PROBABILITY VARIANTS

[76] Inventor: Donald A. Kaplan, 3442 Clay St., San Francisco, Calif. 94118

[21] Appl. No.: 382,843

[22] Filed: May 27, 1982

[51] Int. Cl.[4] .................. C12Q 1/00; C12M 1/16; C12M 1/18
[52] U.S. Cl. .................................. 435/7; 435/4; 435/29; 435/34; 435/291; 435/297; 435/299; 435/810; 436/519
[58] Field of Search ............ 435/291, 299, 7, 29, 435/34, 297, 4, 810; 436/519

[56] References Cited

U.S. PATENT DOCUMENTS

| 3,645,687 | 2/1972 | Nerenberg | 435/291 X |
| 4,326,028 | 4/1982 | Brown | 435/299 X |
| 4,421,849 | 12/1983 | Breuker | 435/29 |
| 4,446,234 | 5/1984 | Russo | 435/29 |

OTHER PUBLICATIONS

D. A. Kaplan et al., Gene, 13(3), 211-220, (Apr. 1981).

Primary Examiner—Sidney Marantz
Attorney, Agent, or Firm—Townsend & Townsend

[57] ABSTRACT

Rapid screening of a large number of organisms for variants producing particular products is accomplished using membrane plates having a predetermined molecular weight cutoff and which divide a container into two chambers. High density cellular lawns are employed in conjunction with labeled antibodies for the product of interest mixed in soft agar. The cells are subjected to viral lysis and after the plaques have reached maturity, the plates are immersed in buffer. Residual soluble labeled antibody diffuses from the agar, and immunoprecipitate of the product and the antibody may then be detected.

7 Claims, 1 Drawing Figure

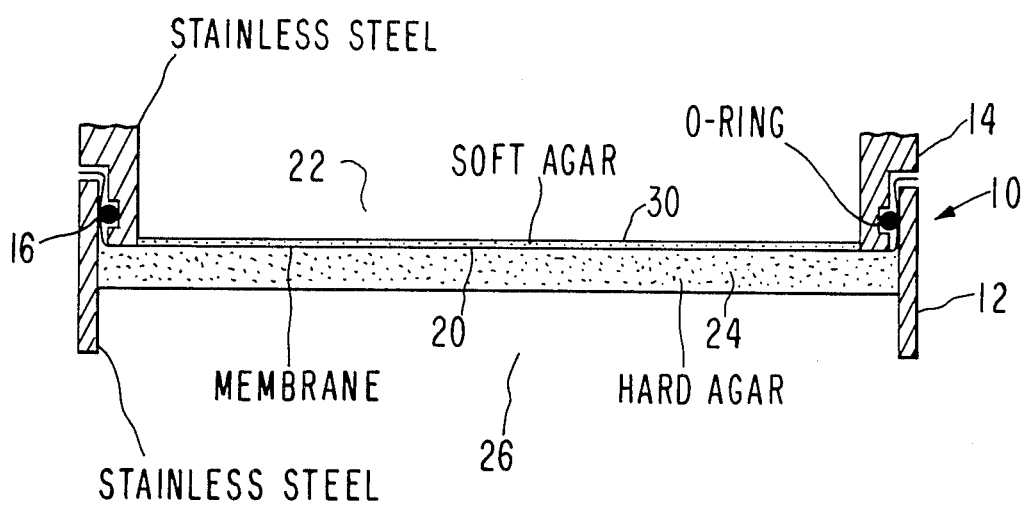

EFFICIENT SCREENING METHODS FOR LOW PROBABILITY VARIANTS

BACKGROUND OF THE INVENTION

1. Field of the Invention

Detection of specific macromolecular species associated with individual cellular colonies or virus plaques is of crucial importance in molecular cloning, screening of conjugants, or transformed or transduced cells, and the like. Existing methods for detecting either specific nucleic acid sequences or antigens are adequate for many situations, but leave much to be desired when one is searching for the rare event. Screening to be successful should be simple and easily performed, minimize false positives and have a substantial assurance of being able to detect the presence of the mutant or variant of interest.

With the ability to prepare antibodies highly specific for a determinant site, one has the opportunity to specifically bind to a protein which serves as a marker for the presence of a cell or virus. The difficulty still remains in trying to detect an extremely small proportion of a total cellular and/or viral population associated with the protein of interest. Desirably, any technique which employs monoclonal antibodies or polyclonal antibodies should be reasonably rapid, allow for accurate discrimination, permit the screening of large numbers of cells or viruses and provide for isolation of the desired variant organism.

2. Description of the Prior Art

Kaplen, et al. Gene (1981) 13:211; and Kaplan, et al., ibid, (1981) 13:221 describes a method for screening large numbers of bacteriophage microplaques for the presence of specific antigen.

SUMMARY OF THE INVENTION

Method and apparatus are provided for rapid screening of a large number of organisms for a low percentage of variants producing a particular variant product or marker, normally a poly(amino acid). The method employs membrane plates which serve to divide a container into two chambers by a membrane which has a predetermined molecular weight cutoff. High density cellular lawns are employed in conjunction with labeled antibodies for the marker mixed in soft agar. The cells are subjected to viral lysis and after the plaques have reached maturity, the plates are immersed in buffer, whereby residual soluble labeled antibody diffuses from the agar. The immunoprecipitate of the marker poly(amino acid) and the labeled antibody may then be detected by conventional ways.

BRIEF DESCRIPTION OF THE DRAWING

The FIGURE is a schematic drawing of a membrane plate.

DESCRIPTION OF THE SPECIFIC EMBODIMENTS

Methods and apparatus are provided for relatively rapidly screening of a large group of organisms, particularly cells and viruses, for the presence of a variant producing a ligand to which a labeled receptor may bind. The method involves creating a thin layer of soft agar containing a high cellular density, a lytic virus, and a labeled receptor. The agar is then extracted with buffer to remove soluble diffusible labeled receptor. The labeled receptor is capable of forming a non-diffusible aggregation with the marker, so that the sites where the variant organism are present, and therefore, where the marker is produced, retains the presence of the labeled receptor. This site may be detected by means of the label and viable cells or viruses isolated, substantially free of other organisms not producing the variant marker.

To detect the variant organisms, either virus or cellular, an aqueous mixture is prepared of the cells at relatively high density, viruses at a concentration which will be conveniently determined empirically, and appropriate salts and the mixture incubated for a short time to allow for the viruses to invade the cells. To the mixture is then added at least a portion of a labeled receptor composition, which may have one or more components, which together provide for a precipitate with the variant, normally antigenic, marker produced by the variant organism. Also added is a gelling agent, normally agar, and the mixture poured to provide a thin layer of soft agar.

After the agar is hardened, the agar is incubated for a sufficient time for lysis to occur. Depending upon the nature of the precipitating receptor composition, the agar may be treated in a variety of ways. Particularly, where polyvalent antibodies are employed, the agar is extracted with buffer to remove any non-precipitating labeled receptor and the agar layer, substantially freed of soluble diffusible labeled antibody by elution with an aqueous medium, is then treated in accordance with the nature of the label to detect the presence of the variant organism.

Desirably, a membrane plate is employed which provides for two chambers, a lower larger chamber and a smaller upper chamber. The chambers are separated by a membrane having a relatively low molecular weight cutoff e.g., $\leq 100,000$, so that diffusion of small, but not large, molecules may occur between the layers. Into the lower portion is introduced a relatively thick layer of the gel, while in the upper portion the thin soft agar layer is introduced which contains the organisms and reagents. In this manner, a stable layer is obtained, but problems associated with a thick gel layer are avoided. The total gel layer thickness will usually be at least 2 mm, more usually at least 2.5 mm and generally there is no advantage in going above 5 mm. The soft agar layer will be about 10 to 20% of the total thickness.

Interest in detecting a variant in an organism population may result from a variety of situations. Particularly, with recombinant DNA technology, one is frequently looking for a conjugant, transductant or transformant which is capable of producing a poly(amino acid) product of interest. In some instances, the poly(amino acid) product will be a fused protein, where the product is fused to a portion or all of an amino acid chain of a different poly(amino acid) product.

The cellular host may vary widely, including prokaryotes and eukaryotes. The eukaryotes may be lower or higher species, such as fungi, protozoa, algae, mammalian, particularly cancerous cells, or the like. The significant factor is that the cells can be grown to relatively high densities in vitro, that there is present a variant cell of interest which produces a poly(amino acid) or other antigenic marker, and that the cells may be lysed by viruses, including bacteriophage. The marker which is produced will be antigenic, having a plurality of binding sites. While normally being a poly(amino acid), polysaccharides, nucleic acids, or other like markers may find use, where available receptors exist.

The concentration of cells in the medium in which the cells and viruses are originally combined will generally be at least about $10^7$ cells/ml, preferably higher, usually not exceeding $10^{10}$, more usually not exceeding $10^9$ cells/ml. The concentration of virus will normally be determined empirically in relation to the nature of the cells and virus. Concentration of the virus will generally range from about $10^2$ to $10^6$ viruses/ml, so that relatively low multiplicities of infection are involved.

The receptor which is employed will normally be a polyvalent antibody or fragment thereof. Various antibodies include IgG, IgM, IgA, IgD and IgE. However, natural receptors exist which also have a plurality of binding sites, which would also find use where the binding affinity is high and the marker is the homologous ligand. Where polyclonal precipitating antibodies against a target antigen are available having high enough affinity, they will normally be used, unless a preferred naturally occurring receptor is available. However, in situations where a fused protein is involved, the antigenic determinant on the fused product may be weak or insufficiently exposed, and combinations of monoclonal and polyclonal antibodies may find use. One could use labeled monoclonal antibodies to the marker and unlabeled polyclonal antibodies to the non-marker fused polypeptide portion. Thus, a non-diffusible labeled aggregation would be formed. Also, one may wish to use nonprecipitating monoclonal antibodies in situations, where the marker of interest may have many common determinant sites with other antigens which may be present. Again, it may be useful to include unlabeled, precipitating polyclonal antibodies against the common determinant sites, where the marker of interest shares determinant sites with other antigens which are present.

Another embodiment is a "sandwich" technique, where the primary receptor for the marker is added, residual soluble primary antibody extracted, followed by addition of secondary receptor which binds to the primary antibody due to haptenic labeling of the primary receptor or because of binding to primary receptor determinant sites, e.g., Fc. The secondary receptor is labeled and acts as the precipitating agent.

In this manner, one is freed of the constraint of requiring the antibody conjugate also to act as an immunoprecipitant. Thus, the labeled monoclonal or polyclonal antibody will be specific for the target moiety of the marker of interest, specifying the presence of the expression of a specific antigenic determinant or determinants.

A wide variety of labels may be employed, some more effectively than others. Various labels include radionuclides, enzymes, fluorescers, enzyme substrates and cofactors, chemiluminescers, etc. Labels of particular interest are those which provide for substantial amplification, such as can be observed with enzymes. The label may be conjugated to the receptor in conventional ways. For illustrative labels see U.S. Pat. Nos. 3,817,837; 3,996,345; 4,039,385; 4,067,774; 4,318,980; etc.

An empirical approach is employed to determine the amount of receptor conjugate required for optimal screening. The optimal concentration depends upon several variables, including the specific activity of the conjugate, the amount of antigen produced per plaque, and the avidity of the antibody for the antigen. The ability of the conjugate to form a non-diffusible aggregation is also an important consideration and should be confirmed, whenever possible.

Included in the medium containing the cells and viruses will be salts, which aid in the viability of the organisms, as well as the viral invasion of the cells. Normally, relatively low concentrations of magnesium and calcium as their chlorides will be employed, generally in concentrations of from about 0.5 to 5 mM. Other additives may also be included in particular situations.

The solution used to extract the soluble diffusible receptor which is not bound to the marker may be any convenient aqueous medium which does not detrimentally affect the viability of the organism of interest. Conveniently, buffered saline may be used, more usually isotonic phosphate buffered saline at about neutral pH (pH 7).

Although feasible, plating of the conjugate-containing soft agar layer directly onto hard agar is not found to yield optimal results. The conjugate diffuses into the hard agar, therefore diminishing the concentration of the label at the site of plaque formation and making removal of unprecipitated conjugate difficult. This problem can be circumvented by using a dialysis membrane interposed between the two agar layers. In this way, diffusion of the conjugate into the bottom agar layer is prevented. The plates are schematically shown in the figure.

The plate 10 has an external ring 12 and an internal ring 14 with an O-ring 16 to inhibit leakage between the two rings. The rings have outer diameters of about 5 to 12 cm with thicknesses of about 0.5 to 2 mm. To prepare the unit, a dialysis membrane 20 is placed between the inner and outer rings 12 and 14 and drawn taut as the two rings are pressed firmly together. Exemplary of the membrane is a membrane, such as Spectraphor 2, having a molecular weight cutoff of about 12,000-14,000, with a dry thickness of about 0.00218 inches.

For the most part, membranes which find use will have cutoffs of less than about 30,000 molecular weight, preferably less than about 20,000 molecular weight, with a thickness in the range of about $5 \times 10^{-3}$–$5 \times 10^{-4}$ inches. Excess membrane may be trimmed away and the assembled unit is conveniently placed in an appropriate petri plate and autoclaved for 10 min. Water is then added to the upper surface of the membrane (shallower compartment 22) prior to autoclaving to prevent drying and cracking of the membrane. After sterilization, the water is removed, the apparatus is inverted, and molten bottom agar 24 added to the exposed (deeper compartment 26) surface membrane. After the agar has solidified, the unit is inverted and used for plating soft agar 30.

The phage adsorption/infection step is performed by adding the appropriate amount of the cell suspension, magnesium and calcium salts, the appropriate amount of viral stock and incubating the mixture at 37° for a sufficient time to allow for viral invasion. Usually 5 to 20 minutes, more usually 10 minutes will suffice. To the mixture is then added an appropriate concentration of the labeled, receptor, normally labeled antibody, or at least a component of the receptor system. Molten agar is then added and the mixture poured directly onto the membrane 20 in the upper chamber 22 of the unit to form soft agar layer 30. After the top soft agar layer 30 has hardened, the plates are inverted and incubated for a sufficient time, conveniently overnight at 37° C.

In determining the concentration of phage, it is generally desirable to plate the phage at relatively low density, approximately 100,000 per plate, (9 cm diameter). With greater experience and depending upon the particular detection system, higher levels of phage may be employed. In determining the cell density, two different approaches may be employed. One can divide the total area of the plate by the average number of plaques under the plating conditions employed. The number obtained divided by three is in about the right range of the number of plaques that can be accommodated without detrimental losses of antigen per plaque.

Alternatively, one may use an equation derived by Kaplan, et al., supra, which predicts the fraction of nonintersecting plaques, p as a function of the total number of plaques of average radius r per plate of radius R. A conservative value for p is 0.5.

To remove the diffusible labeled receptor, that is, the label receptor which is not involved in a non-diffusible aggregation, the bottom agar 24 is first removed gently from the lower chamber 26 of the membrane-plate unit 10 with the aid of a small spatula, and the units are placed in a container containing an aqueous buffered solution, for example, phosphate buffered saline, and the top agar immersed in the solution. To minimize trapping of air in the lower chamber 26, the plates are initially inserted in a vertical orientation and are then placed horizontal on the bottom of the container with the soft agar layer uppermost. The container is incubated at low temperatures for an extended period of time, generally at about 4° C. for about 8 to 14 hours, while the buffer is kept in gentle motion against the unit surfaces, either by agitation with a magnetic stirring bar or by slow rocking or rotation of the container. Promptly after removal of the plates from the buffer, where one is concerned with developing an observable response, the plate is treated with the necessary reagent(s) to produce the response.

When non-temperate phage are employed a small glass capillary (ca. 0.2 mm inside diameter) can be employed for recovery of the phage. The capillary is inserted into the center of the labeled area and the retreived core of top agar is free suspended in an appropriate buffer. The mixture may then be replated in an appropriate medium.

Various modifications of the above described method may be employed, depending on particular situations, such as the nature of the marker, the nature of the available receptors, and the like. In some situations, the method can be modified, but at some cost to accuracy and efficiency.

While the membrane plates give superior results, acceptable results may be obtained with conventional plating methods. However, a number of precautions must be followed. It is important that the thickness of the bottom agar be at least 3 mm in order to obtain maximal growth of the bacterial layer. If plastic petri plates are used, they must be fixed with double-sided adhesive tape to the bottom of the elution chamber, the diffusible labeled receptor extractant chamber, before the aqueous buffer is added. The elution or extraction is usually carried out over forty-eight hours, with one change of buffer. Although the background is never found to be as low in conventional plates as in membrane plates, with an enzyme label, the background may be minimized by initiating the chromogenic reaction immediately (within seconds) after removal of plates from the elution medium. While soluble labeled conjugate is never completely removed from the hard agar layer, the concentration is minimal in the soft agar layer immediately adjacent to the elution fluid. If the chomogenic reaction is performed quickly, the diffusion of the labeled receptor conjugate to the surface is minimized.

To prevent the deleterious effects of plaque intersection on antigen production at high plaque densities, plaque size must be kept small. By plating viruses in the presence of sufficiently high concentrations of cells, the period during which cells are infectable is reduced; hence fewer generations of viral multiplication occur. With Charon 17 phage, plated on $E.\ coli$ LA108, plaque radius decreased logarithmically as the initial cell density was raised from $9 \times 10^6$ cells/ml to $9 \times 10^8$ cells/ml. At cell concentrations greater than $3 \times 10^9$ ml, plaques were no longer visible under a dissecting microscope at 60x. Other factors to be considered affecting plaque size are the nature of the cells, the nature of the virus, and the type of medium which is employed.

While with TYE medium difficulties were experienced in peforming the adsorption/infection step with the above phage and bacteria, a hybrid medium, consisting of 10 g/l Difco Tryptone, 2 g/l Difco extract and 5 g/l NaCl proved to be superior.

For convenience, the various materials used for the determination may be combined as a kit. The kit would conveniently have the membrane plate and additional membrane sheets. Also, an enzyme composition would be provided which has a substrate which produces a chromogenic product. Desirably, the enzyme would be functionalized for ease of conjugation to a receptor, e.g., antibody. For example, horse radish peroxidase could be periodate cleaved to produce aldehydes, which with sodium cyanoborohydride would provide for amine linkage. The enzyme could be functionalized with p-carboxybenzenediazosulfonate, p-maleimidobenzoic acid, p-maleimidobenzenediazo chloride, etc. Also included could be substrates, mixtures of magnesium and calcium chlorides in about 1:1 molar proportions, buffers, ancillary reagents, e.g., agar, etc.

The following examples are offered by way of illustration and not by way of limitation.

EXPERIMENTAL

Chromogenic Screening of λ Phage Microplaques

The following protocol was used to screen for specific antigen (β-galactosidase) in the coliphage λ system.

Buffers:

PBS: 8 g NaCl; 2.17 g $Na_2HPO_4.7H_2O$; 0.2 g $KH_2PO_4$ 0.2 g KCl; water to 1 liter.

PBS: 10 mM Tris-HCl, pH 7.5; 0.1M NaCl; 10 mM $MgCl_2$; 0.05% gelatin.

λ dilution buffer: 10 mM Tris-HCl, pH 7.5; 10 mM $MgSO_4$.;

17.5 mM sodium phosphate, pH 8: per liter, 10 ml 0.875M $Na_2HPO_4.7H_2O$, 10 ml 0.875M $NaH_2PO_4.H_2O$.

0.1M sodium phosphate, pH 6.8: per 100 ml, 5.83 ml 0.875M $NaH_2PO_4.H_2O$, 5.6 ml 0.875M $Na_2HPO_4.7H_2O$.

1M carbonate-bicarbonate buffer: to make 100 ml, 30 ml 1M $Na_2CO_3$, 70 ml 1M $NaHCO_3$.

Chemicals:

DAB 3,3'-diaminobenzidine. Sigma No. D5637.

TMB: 3,3',5,5'-tetramethylbenzidine. Sigma No. T.2885.

Diethylaminoethyl cellulose: Whatman DE-52, preswollen microgranular anion exchanger, Whatman Cat. No. 4057-050.

Sephadex G-25, fine. Pharmacia Fine Chemicals Item 17-0032-02.

IPTG: Isopropyl-$\beta$-D-thiogalactopyranoside. Sigma No. I-5502.

Glutaraldehyde: Grade 1 specially purified. 25% aqueous solution. Sigma No. G-5882.

$H_2O_2$: Superoxol, 30% with 1 ppm $Na_2SnO_3.3H_2O$ as preservative. Baker 1-2186.

3-Amino-9-ethylcarbazole. Sigma A-5754.

Dimethyl sulfoxide. Sigma D-5879.

Enzymes:

$\beta$-galactosidase.

Horse radish peroxidase: hydrogen-peroxide oxidoreductase; EC 1.11.1.7. Type VI salt-free power. Sigma No. P-8375.

Media:

Broth: 10 g Difco tryptone, 2 g Difco yeast extract, 5 g NaCl, 1 liter water. Sterilize by autoclaving. When cool add 1/100 volume of 10% maltose.

Plates: 10 g Difco tryptone, 2 g Difco yeast extract, 5 g NaCl, 15 g Difco agar, 1 liter water. Sterilize by autoclaving. When IPTG is needed, allow liquid to cool to 55° C. and add 0.12 g IPTG per liter (0.5 mM final concentration). Fill standard glass petri plates about half full, or add 8 ml to 52×15 mm plastic petri plates: (Falcon No. 1007). Allow to cool.

Top Agar:

10 g Difco tryptone, 2 g Difco yeast extract, 5 g NaCl, 7.5 g Difco agar, 1 liter water. Sterilize by autoclaving. Melt agar prior to use and keep molten at 55° C. At time of addition of phage and cells, add 10 $\mu$l 50 mM IPTG per ml of top agar.

Phage:

Charon 17 (Williams and Blattner) J. of Virol. (1979) 29:555): $\lambda$ lac5 sRI3° cIam sRI4° nin5 sHindIII6° DK1.

Charon 30 (Rimm et al., Gene. (1980) 12:301). $\lambda$ B1007 KH54 nin5 s(BamHI 2-3 B1007)+ DK1 sR14°.

$\lambda$70 (Charnay et al., Nature (1980) 286:893): $\lambda$ plac 5-1 UV5 imm$\lambda$ nin5 HBs-1.

cI 857 (Sussman and Jacob, Compt. Rend. (1962) 254:1517).

Bacterial strains:

LA108: F- ton A $\Delta$(lac)×74 nal supE supF rk−mk+. (Pourcel et al., Molec. Gen. Genet. (1979) 170:161.

MC4100: F− araD139 $\Delta$(lac)U169 rpsL relA thi. (Received from N. Sternberg).

MC4100: F' lacIq. F' lacIq araD139 $\Delta$(lac)U169 rpsL relA thi. (Received from N. Sternberg).

Preparation of anti-$\beta$-galactosidase antibody:

Six month old New Zealand white rabbits were used. $\beta$-galactosidase was stored at −70° C. in 10 mM Tris-HCl, pH 7.5 at a concentration of 10 mg/ml. For the primary injection, 100 $\mu$g of enzyme was dissolved in 1.5 ml of PBS, and an equal volume of complete Freund's Adjuvant (Difco No. 0638-60) was added. Half the dose was given subcutaneously and half intramuscularly. This initial injection was followed by bimonthly secondary injections performed in the same manner except that incomplete Freund's Adjuvant (Difco No. 639-60) was used in place of complete adjuvant. Rabbits were bled (40-50 cc of whole blood) bimonthly.

Antibody was prepared from the serum by ammonium sulfate precipitation and DEAE-cellulose chromatography in a manner similar to that described by Garvey, et al., in methods in Immunology, Benjamin/Cummings Publications Co., Pending, Mass. (1977) p215. The fraction precipitated at 40% saturation ammonium sulfate was resuspended and dialyzed extensively against 17.5 mM sodium phosphate, pH 6.8. It was then chromatographed on a 2.6 cm×11 cm DEAE-cellulose column in the same buffer. Immunoreactive fractions were pooled, precipitated with 40% saturation ammonium sulfate and dialyzed extensively against 0.15M NaCl. The purified immunoglobulin was then stored at −70° C. The yield was ca. 5.4 nanomoles immunoglobulin per ml serum.

Conjugation:

Antibody was conjugated to horse radish peroxidase by the method of Avrameas and Ternynch, Immunochemistry (1971) 8:1175, with few modifications. Horse radish peroxidase (200 mg) was resuspended in 2 ml 0.1M sodium phosphate, pH 6.8, 1.25% glutaraldehyde and incubated in the dark at room temperature for 18–12 hours. It was then chromatographed on a 2.6 cm×11 cm Sephadex G-25 column equilibrated with 0.15M NaCl at room temperature. The brown-colored fractions were pooled and the volume brought to 20 ml with 0.15 NaCl. An equal volume of anti-$\beta$-galactosidase antibody (70 mg) in 0.15M NaCl was added, followed by a 1 ml of 1M carbonate bicarbonate buffer, pH 9.6. After 24 hours incubation at 4° C., lysine was added to 2M, and the mixture was incubated an additional 2 hours at 4° C. and then extensively dialyzed against PBS. An equal volume of saturated ammonium sulfate (pH 7.6) was added, and the mixture was slowly stirred for 30 min on ice. After 16 hours at 4° C. the mixture was centrifuged at 7,700 xg for 20 min. The pellet was resuspended in 20 ml PBS, and the ammonium sulfate precipitation step was repeated. This second pellet was resuspended in 4 ml PBS and extensively dialyzed against PBS. The conjugate preparation was partitioned in 1 ml aliquots and stored at −70° C.

Horse radish peroxidase in the conjugate was estimated from the $A_{403}$ (an $A_{403}$ of 1 is equivalent to 0.4 mg/ml HRP; Worthington). The $A_{280}$ contributed by horse radish peroxidase was estimated to be $\frac{1}{3} \times A_{403}$. The amount of antibody in each preparation (in mg/ml) was calculated by subtracting from the $A_{280}$, the contribution by horse radish peroxidase at this wave length, and dividing by 1.46. The yield with this procedure is usually about 0.23 mg of horse radish peroxidase conjugated per mg of antibody (0.9 molecules HRP per antibody molecule).

Phage Lysates:

Phage stocks were prepared according to Miller, in, Experiments in Molecular Genetics, Cold Spring Harbor Laboratory, Cold Spring Harbor, New York, (1972) p. 37. Following two sequential plaque purifications, the phage from a single plaque were resuspended in 0.2 ml BSP buffer, adsorbed to E. coli strain LA 108 and plated onto 9 cm plates. After 8 hours growth at 37° C., 4 ml of medium containing 10 mM $MgSO_4$ was added, and the plates were incubated at 4° C. for 16 hours. The liquid and soft agar were collected by scraping the plate, and the soft agar was removed by centrifugation. Phage stocks were stored at 4° C. over chloroform.

Preparation of Cells:

Overnight cultures were prepared by adding 0.1 ml of a −20° C. glycerol stock to 20 ml broth and incubating with shaking at 37° overnight. Cultures to be used for infection are initiated by adding 5 ml of the overnight culture to 50 ml broth in an 250 ml Erlenmeyer flask and incubating 5-8 hr at 37° on a rotary shaker. The density of the culture is then determined by measuring the optical density at 540 nm (1.0 optical density unit at 540 nm is equivalent to $1.2 \times 10^9$ cells per ml), and the cells are used immediately for plating.

Membrane plates are available in reusuable stainless steel or disposable plastic versions from Genetic Sciences, Inc., P.O. Box 25829, Los Angeles, CA 90025. To prepare the plates, a 12 cm piece of dialysis membrane (Spectrapore 2, see previous description) is moistened, placed between the two halves of the plate and drawn taut as the two halves are pressed firmly together. Excess membrane is trimmed away and the assembled plate is placed in a 9 cm glass petri plate and autoclaved for 10 min. Water (5 ml) is added to the upper surface of the membrane (shallower compartment) prior to autoclaving to prevent drying of the membrane. After sterilization the water is removed, the apparatus is inverted, and 12 ml molten bottom agar is then added to the exposed (deeper) compartment after the agar has solidified, the plates are inverted and used for plating soft agar as described below.

Plating of Phage:

The phage adsorption/infection step is performed by adding 0.05 to 0.16 ml of cell suspension, and 0.16 ml of a solution 10 mM in $MgCl_2$ and 10 mM in $CaCl_2$, to 0.16 ml of appropriately diluted phage stock, and incubating the mixture at 37° C. for 10 minutes. Then 16 μl of 50 mM IPTG, 20-50 μl of HRP-Ab conjugate, and 1.6 ml molten top agar (55° C.) are added, and the mixture is poured directly onto the membrane in the upper chamber of the membrane plates. After the top agar has hardened, the plates are inverted and incubated in 9 cm glass petri plates overnight at 37° C.

Removal of unprecipitated conjugate: "dialysis":

To remove unprecipitated conjugate, the bottom agar is first removed gently from the lower chamber of the membrane-plate with the aid of a small spatula, and the plates are placed in a 27 cm $\times$ 32 cm $\times$ 12 cm rectangular plastic container containing 4 L PBS. To minimize trapping of air in the lower chamber, the plates are initially inserted in a vertical orientation, and are then placed horizontal on the bottom of the container with the soft agar layer uppermost. The container is incubated for 4° C. for 8-14h, while the buffer is kept in gentle motion across plate surfaces either by agitation with a magnetic stirring bar or by slow rocking or rotation of the container.

Color development: the chromogenic reaction:

The chromogenic reaction is performed immediately after removal of plates from the liquid. To a freshly prepared solution of DAB (0.5 mg/ml in PBS) is added $H_2O_2$ to a final concentration of 0.015%, and 8 ml of the mixture is added immediately to each plate. Brown HRP reaction product ("stain") is apparent within 2-3 minutes. Color is fully developed by 10 minutes; at that time the plates are rinsed to remove substrate.

Retrieval of lysogens or phage:

The minute "stained" plaques obtained with high indicator cell densities are most easily detected with the aid of a disecting microscope (magnification 30-60X). When phage capable of lysogenization are used, lysogens formed within plaques may be retrieved by inserting a sterile wooden toothpick into the center of the stained area. Material on the tip is resuspended in 1 ml of medium. Plating of 0.2 ml of a 1:10 diultion yields 500-2000 colonies, ca. 1% of which are antigen-positive. When non-temperate phage are employed a small glass capillary (ca. 0.2 mm inside diameter) is used, prepared by drawing out the tip of a pasteur pipet heated in a flame. The capillary is inserted into the center of the stained area, and the retrieved core of top agar is resuspended in 0.2 ml BSP buffer. To this are added 0.1 ml 10 mM $MgCl_2$, 10 mM $CaCl_2$ and 50-100 μl cell suspension; and the mixture is replated as above. When sampling of antigen-positive plaques was performed on plates containing high densities of antigen-negatives (initial concentration in the soft agar $1.2 \times 10^3$ phage/ml), the retrieval process usually gave $1-2 \times 10^4$ isolated plaques with ca. 1% showing an antigen-positive reaction.

Gene expression within phage infected cells and stability of the antigenic product:

The effect of the lac inducer IPTG (isopropyl-β-D-thiogalactoside) on β-galactosidase production in plaques of Charon 17 phage formed on two E. coli strains was examined: MC4100-F'lacIq, which produces multiple copies of the lac repressor, and MC4100, which lacks repressor. The diameters of stained immunoprecipitin rings were measured and areas calculated. With strain MC4100 a high level of β galactosidase was detected, and the level did not vary within a range of IPTG concentrations from 0 to 5 mM. In contrast, plaques on strain MC4100-F'lacIq contained no detectable β-galactosidase in the absence of IPTG. At 0.1 mM IPTG the strain produced 13% of the β-galactosidase produced in the absence of the episome, and at 0.5 mM it produced 30% of the level.

A fused protein was studied using λ-70, a clone that produces a hybrid protein consisting of the first 1,005 amino acids of β-galactosidase followed by 192 amino acids of the hepatitis B surface antigen. When the soft agar contains only the HRP-conjugate of an anti-hepatitis B surface antigen antibody, no chromogenic immunoprecipitate was detected. However, when unconjugated anti-β-galactosidase was included, rings of immunoprecipitate were formed and the area of the rings correlated with the amount of unlabeled anti-β-galactosidase present. This result supports the fact that the anti-β-galactosidase antibody acts as an immunoprecipitant, facilitating detection of weak hepatitis determinants on the hybrid molecule.

Detection of β-galactosidase in plaques of Charon 17 bacteriophage:

Approximately 65 Charon 17 (λLacZ+) and 46 Charon 30 (λLacZ−) phage were plated in top agar containing $1.7 \times 10^8$ cells/ml E. coli LA 108 and 300 μg/ml conjugate (52 mm plastic petri dish). After incubation at 37° C. for 12.5 hours, the plates were "eluted" for 49 hours and then developed as described in the text. The plate was illuminated from below with light filtered through a Wratten No. 61 green filter and photographed at 2x magnification. The Charon 17 plaques which produce β-galactosidase are surrounded by rings of pigment while the Charon 30 plaques are not.

Effect of media on growth of E. coli:

E. coli strain LA 108 was plated at an initial cell density of $7.9 \times 10^7$ cells/ml in top agar on 52 mm plastic petri dishes containing different media and incubated at 37° C. At various times the plates were scanned in an electrophoresis/TLC densitometer (Quick Scan R and D, Model R4-077; Helena Laboratories) with a 570 nm filter. The number of cells per 5 cm plate was determined from a standard curve derived by measuring the absorbance of plates containing various numbers of cells plated in soft agar. Media: TYE (15 g/L, Difco tryptone; 10 g/l, Difco yeast extract; 5 g/l NaCl); hybrid medium (10 g/l, Difco tryptone; 2 g/l Difco yeast extract; 5 g/l NaCl); and λ medium (media: 10 g/l Difco tryptone; 5 g/l NaCl). The hybrid medium was found to provide the most rapid multiplication and highest number of cells at eight hours.

Effect of plaque density on the efficiency of detection of low-frequency antigen-positive plaques in a large population of antigen-negatives:

Approximately 78 Charon 17 (λLacZ+) phage plated with varying numbers of Charon 30 (λLacZ−) phage on 52 mm plastic petri plates. The top agar contained 300 μg/ml conjugate and an initial indicator cell density of $1.7 \times 10^8$ cells/ml of E. coli strain LA108. After overnight incubation at 37° C. the plates were dialyzed and developed. The number of antigen-positive plaques detected by eye were counted.

| Number of LacZ⁻ phage added | Plaques scored as Lac z | Percent of expected |
|---|---|---|
| $9.2 \times 10^3$ | 78 | 100% |
| $3.7 \times 10^4$ | 77 | 99% |
| $1.1 \times 10^5$ | 63 | 81% |
| $5.9 \times 10^5$ | 52 | 67% |

The above results demonstrate that the subject method and apparatus provide for a highly efficient screening technique for detecting the presence of an antigenic marker produced by an organism, where a variant organism is present among a large number of other similar organisms, which lack the capability for producing the marker of interest. By following the methodology described, one can insure detection of the organism of interest, as well as the ability to isolate and clone the organism substantially free of the other organisms. Substantial enhancement in concentration of the desired organism can be achieved, and if necessary, the subject process may be repeated, with the greatly enhanced ratio of the desired organism to the total number of organisms to insure the capability to clone the desired organism free of the contaminating organisms. The protocol is relatively simple and the results can be attained rapidly, generally within one day. The method can be used with recombinant DNA technology, screening for mutagens, screening for variant species or strains, or the like.

Although the foregoing invention has been described in some detail by way of illustration and example for purposes of clarity of understanding, it will be obvious that certain changes and modifications may be practiced within the scope of the appended claims.

What is claimed is:

1. A method for screening organisms selected from the group consisting of viruses and cells, the viruses and cells being related in that the viruses are capable of lysing the cells, wherein said organisms may include a variant organism producing an antigenic marker, said method comprising combining in a gel: (1) said cells, (2) said viruses, and (3) a labeled receptor composition for said antigenic marker, under conditions where said labeled receptor composition and said marker combine to result in a non-diffusible aggregation;

extracting labeled receptor which is not bound in said non-diffusible aggregation from said gel; and detecting said label in said gel at a location, said variant organism being present at that location.

2. A method according to claim 1 wherein said label is an enzyme.

3. A method according to claim 2, wherein said cells are bacteria and said viruses are phage.

4. A method according to any of claims 1, 2 or 3, wherein said gel is comprised of a thick gel lower layer substantially free of labeled receptor and a thin gel upper layer containing said labeled receptor and separated by said lower layer by a membrane having a molecular weight cutoff below the molecular weight of said labeled receptor.

5. An apparatus for use in screening organisms comprising an outer ring, internal to said outer ring, an inner ring extending into said outer ring only a portion of the height of said outer ring, said inner ring having an outer circumferential groove, an O-ring in said groove, and a membrane extending across the inner ring, with its outer portion locked between said inner and outer rings, said membrane having a molecular weight cutoff of less than about 100,000.

6. A kit comprising an apparatus according to claim 5, a multiplicity of membrane sheets, an enzyme composition capable of producing a chromogenic product and functionalized for covalent linking to an antibody.

7. A method for screening organisms selected from the group consisting of cells and viruses capable of lysing the cells, wherein said organisms may include a variant organism producing an antigenic ligand, said method employing a screening apparatus including a membrane having a preselected molecular weight cutoff which defines two chambers, said method comprising:

combining said cells and said viruses in a liquid gel;

pouring said liquid gel into one chamber of the screening apparatus to form first gel layer;

forming a second gel layer in the other chamber either before or after said first gel layer has been formed, said second gel layer being free from cells and viruses;

exposing the first gel layer to diffusible labeled antibody specific for the marker, whereby non-diffusible labeled aggregations are formed in the presence of said antigenic ligand;

removing said second gel layer;

extracting the diffusible labeled antibody from the first gel layer by immersion in an aqueous solution; and detecting said label in the first gel layer at a location which is indicative of the presence of said variant organism at that location.

* * * * *